(12) United States Patent
Keller et al.

(10) Patent No.: US 7,422,328 B2
(45) Date of Patent: *Sep. 9, 2008

(54) STERILE HAND HELD SLIT LAMP COVER AND METHOD

(75) Inventors: Amy B. Keller, Sunnyvale, CA (US); John Weberg, Gilroy, CA (US)

(73) Assignee: AMO Manufacturing USA, LLC, Santa Ana, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 11/123,962

(22) Filed: May 6, 2005

(65) Prior Publication Data

US 2006/0250796 A1 Nov. 9, 2006

(51) Int. Cl.
*A61B 3/10* (2006.01)
(52) U.S. Cl. ............... 351/214; 351/218; 351/221
(58) Field of Classification Search ......... 351/200–223, 351/246, 243; 362/257, 274, 804
See application file for complete search history.

(56) References Cited

U.S. PATENT DOCUMENTS

| | | | |
|---|---|---|---|
| 4,838,679 A | 6/1989 | Bille | |
| 4,920,467 A | 4/1990 | Honsberger | |
| 5,293,532 A | 3/1994 | Marshall | |
| 5,342,351 A | 8/1994 | Blaha et al. | |
| 5,413,555 A | 5/1995 | McMahan | |
| 5,437,658 A | 8/1995 | Muller et al. | |
| 5,828,439 A | 10/1998 | Ueno | |
| 5,861,939 A | 1/1999 | Heacock | |
| 6,063,108 A | 5/2000 | Salansky | |
| 6,183,086 B1 | 2/2001 | Neubert | |
| 6,319,273 B1 | 11/2001 | Chen et al. | |
| 6,357,877 B2 | 3/2002 | Takada | |
| 6,547,394 B2 | 4/2003 | Doherty | |
| 2003/0053310 A1 | 3/2003 | Sommers | |
| 2003/0058405 A1 | 3/2003 | Cornsweet et al. | |
| 2005/0024587 A1 | 2/2005 | Somani | |
| 2005/0099602 A1* | 5/2005 | Spediacci et al. | ........... 351/214 |

OTHER PUBLICATIONS

Brochure. SO-801 Hand-held Slit Lamp: Specifications. Scan Optics. 2 pages.
SO-801 Hand-held Slit Lamp User Manual: Instructions and Specifications. Scan Optics (1999) 47 pages.

* cited by examiner

*Primary Examiner*—Ricky L Mack
*Assistant Examiner*—Brandi N Thomas
(74) *Attorney, Agent, or Firm*—Townsend & Townsend & Crew LLP; Mark D. Barrish

(57) ABSTRACT

A sterile barrier is provided for use with a slit lamp. The slit lamp has a proximal handle and a distal light slit transmitting window. The sterile barrier comprises a flexible tubular membrane having a first end, a second end, and an opening therebetween. The opening may be larger adjacent the first end than a handle of the slit lamp. A resilient band is attached to the first end of the tubular membrane. The first end and resilient band in a resiliently expanded configuration are sufficiently large to receive the handle proximally therethrough. The resilient band in the relaxed configuration will releasably restrain the sterile barrier from moving proximally off the handle.

7 Claims, 9 Drawing Sheets

STERILE HAND HELD SLIT LAMP COVER AND METHOD

CROSS-REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

BACKGROUND OF THE INVENTION

This invention relates generally to medical devices, systems, and methods, and more particularly to sterile drapes or covers for slit lamps used to illuminate and view an anterior segment of an eye.

Slit lamps are used in ophthalmic applications to view an anterior segment of an eye with a beam of light. The anterior segment of interest typically comprises a cornea, an iris, a sclera, an anterior lens capsule, a posterior lens capsule, and/or a lens nucleus. A beam of light can illuminate these tissues while an operator views the illuminated area by direct examination or through a magnification optic such as a microscope.

The beam of light from a slit lamp can have a varying beam cross section. For example, in some instances the beam is desirably focused to form a narrow slit. Such a beam is desirable for examining layers of a cornea of an eye. In other instances, for example when viewing a large area of an eye, an operator adjusts the beam to have a wide beam cross section. Slit lamps often pass light through a slot aperture. The variation in size of the light beam can be, for example, accomplished by mechanically changing a width across a slot aperture.

During LASIK refractive laser surgery a surgeon generally makes a corneal flap with a microkeratome. The surgeon is typically gloved and sterile during LASIK. After a flap is lifted, the refractive laser treatment is performed on the underlying stroma, and then the flap is laid back onto the stromal bed. The refractive laser surgeon will often move the patient from the laser system treatment chair to a commercial slit lamp, where the surgeon evaluates repositioning of the LASIK flap. The beam from the slit lamp may also be well suited for viewing any debris under the LASIK flap, and for viewing any wrinkles in the LASIK flap. Debris and flap wrinkles can then be appropriately treated and corrected.

U.S. patent application Ser. No. 10/876,268, filed on Jun. 23, 2004 and entitled "Sterile Hand Held Refractive Surgery Slit Lamp Illumination System" (the full disclosure of which is incorporated herein by reference) describes a slit lamp system which may be particularly well suited for laser eye surgery. While this system may present significant advantages for use in examining refractive tissues within a sterile field associated with refractive surgery, still further advancements and improvements might be desirable. In particular, known sterile surgical covers may not be ideally suited for use during laser eye surgery and ophthalmic examinations. In general, sterile covers providing improved ease of use without compromising sterility and without increasing complexity or costs would be beneficial.

BRIEF SUMMARY OF THE INVENTION

In an first aspect, the invention provides a sterile barrier for use with a slit lamp. The slit lamp has a proximal handle and a distal light slit transmitting window. The sterile barrier comprises a flexible tubular membrane having a first end, a second end, and an opening therebetween. A resilient band is attached to the first end of the tubular membrane so that an opening of the resilient band is substantially coextensive with the opening adjacent the first end. The resilient band has a relaxed configuration and resiliently expanded configuration. The resilient band in the relaxed configuration is as small or smaller than the cross-section of the slit lamp between the handle and the window so that the resilient band will releasably restrain the sterile barrier from moving proximally off the handle.

In many embodiments, the slit lamp will have one more slidable inputs for varying characteristics of slit light from the window. The tubular member will often be configured for manual movement of the slidable inputs through the tubular membrane. The tubular membrane may comprise a material that inhibits rustling sounds during slidable input movement.

In many embodiments, the sterile barrier may comprise a tapering tube of polyurethane, polyethylene, or cast polyethylene. Preferably the tubular membrane comprises polyurethane.

The first end of the tubular membrane may be defined by a fold, with the resilient band being disposed between an inner layer of membrane material and an outer layer of membrane material, the inner and outer layers separated by the fold. A proximal portion of the tubular membrane near the second opening may fittingly receive the handle therein with sufficient tightness to facilitate secure manipulation of the slit lamp while grasping the handle through the proximal portion. A distal portion of the tubular membrane may be sized to allow local movement of membrane material with movement of a variable position sliding input of the slit lamp while the slit lamp adjacent to the sliding input is disposed within the distal portion.

In another aspect, the invention provides a method comprising inserting a handle of a slit lamp proximally through a first end of a flexible tubular sterile membrane. Distal movement of the first end of the tubular membrane from the slit lamp is restrained by direct or indirect engagement forces between: the slit lamp between the handle and a slit light transmitting window; and a resilient band of the tubular membrane.

Other aspects of the invention may comprise a system including any of the slit lamps and tubular membranes described herein.

DETAILED DESCRIPTION OF THE INVENTION

Figure 1:
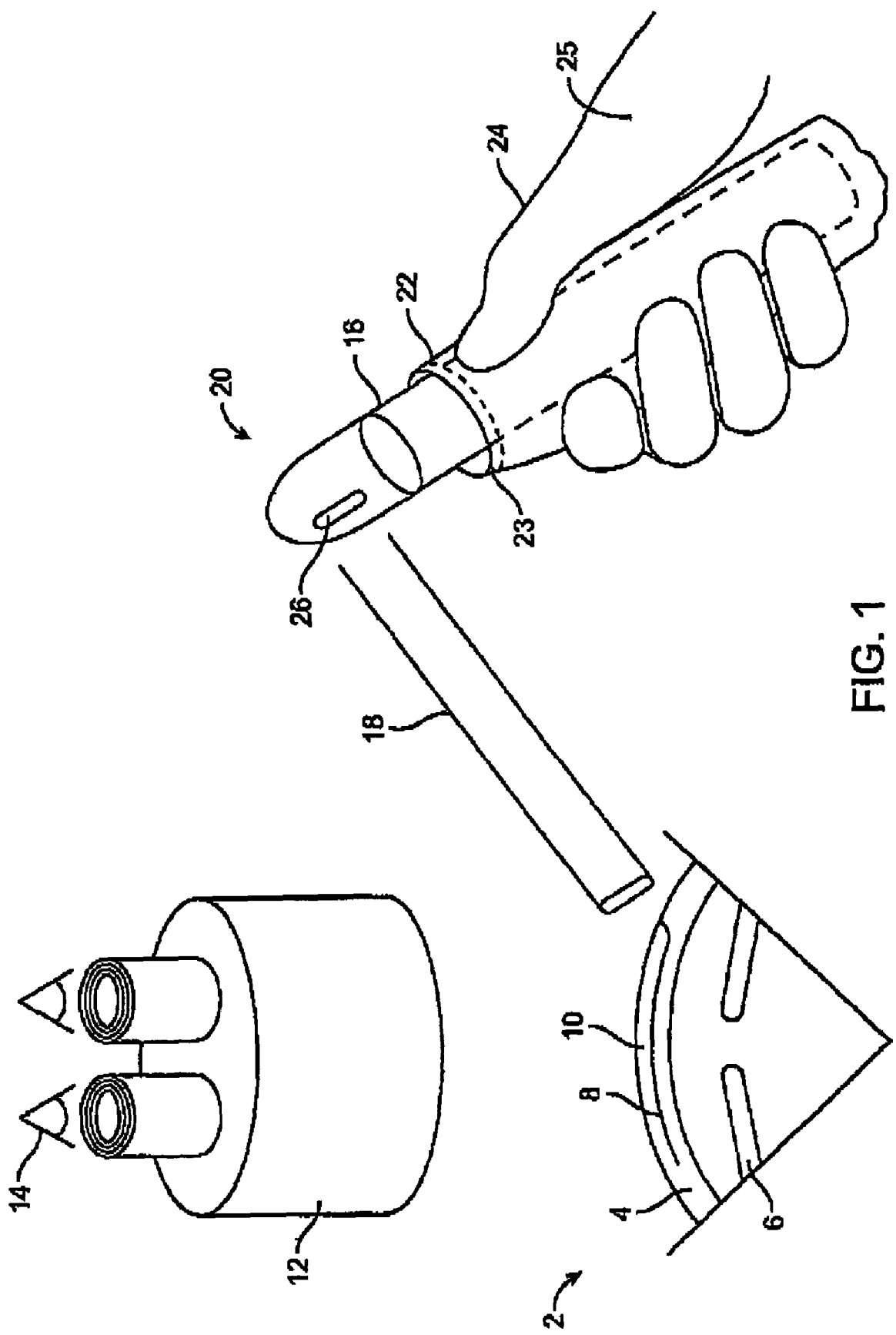
FIG. 1 illustrates a hand held sterile slit lamp system and method for its use in which a sterile cover facilitates variably illuminating an eye during LASIK eye surgery.

As illustrated in FIG. 1, a hand held sterile slit lamp system includes a hand held slit lamp 20 held by a hand 25 of an operator 14 and an operating microscope 12 in accordance with an embodiment of the invention. A sterile glove 24 covers the hand 25 of the operator 14. A sterile flexible disposable cover 22 covers a handle 16 of the hand held slit lamp 20. A beam of light 18 passes through a window 26 of the hand held slit illuminator and illuminates an eye 2. Eye 2 includes a cornea 4, and an iris 6. An incision 8 in cornea 4 is covered by a LASIK flap 10 following cutting with a microkeratome. Operating microscope 12 enlarges a size of eye 2 as seen by operator 14.

In the schematic illustration of FIG. 1, hand held slit lamp 20 is shown extending from a first opening 23 of flexible cover 22. In actual use, flexible cover 22 at first end 23 will often be resiliently biased to a nominal size that is smaller than the adjacent slit lamp, so that engagement between the flexible cover and the slit lamp between handle 16 and window 26 helps to restrain the flexible cover in place. Hence, some or all of the hand held slit lamp adjacent the first end 23 may actually be tightly covered by flexible cover 22 during use. Nonetheless, hand 25 will preferably be free to operate controls of hand held slit lamp 20 through cover 22 during use.

Microscope 12 is often integrated into a refractive laser surgery workstation. The refractive laser surgery workstation preferably comprises a VISX STAR S4™, which is commercially available from VISX, INCORPORATED of Santa Clara, Calif. In alternate embodiments, the refractive laser surgery workstation may comprise any refractive laser surgery workstation. Examples include the VISX STAR™, STAR S2™, STAR S3® Excimer Laser Systems, which are commercially available from VISX, INCORPORATED of Santa Clara, Calif. Other laser systems include those manufactured by ALCON SUMMIT, BAUSCH & LOMB, CHIRON TECHNOLAS, LASERSIGHT, ZEISS-MEDITEC, SCHWIND, WAVELIGHT TECHNOLOGIES, and the like. Optionally, a charger or other components of the slit lamp system may be integrated into the refractive laser system as more fully described in U.S. patent application Ser. No. 10/876,268, previously incorporated herein by reference.

Figure 2:
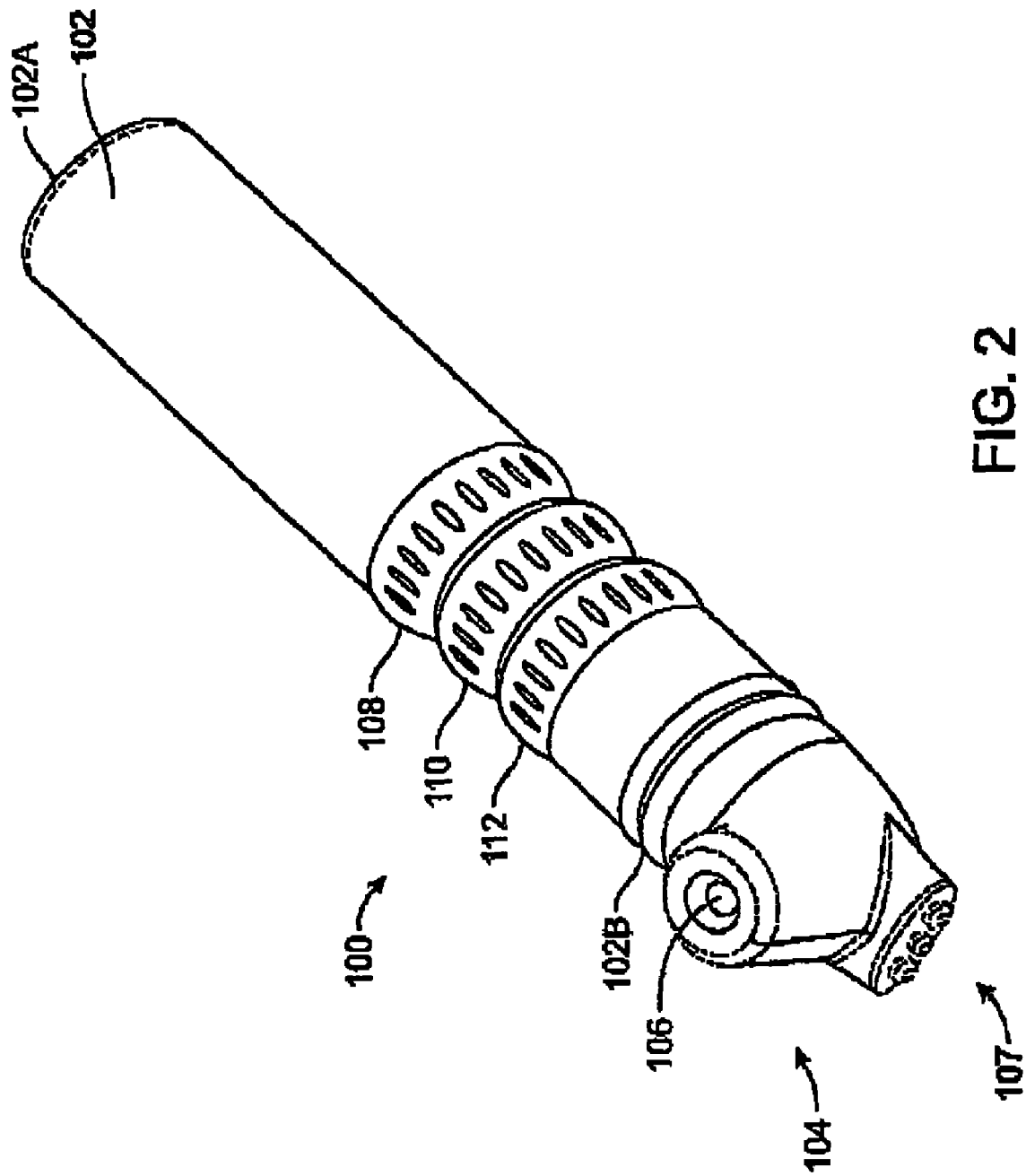
FIG. 2 illustrates a hand held slit lamp of the system and method of FIG. 1.

As illustrated in FIG. 2, a hand held slit lamp 100 includes a handle 102 and a head 104 in accordance with an embodiment of the system. Handle 102 includes a proximal end 102A and a distal end 102B. Head 104 includes a window 106 passing a light beam, and electrical contacts 107 passing electrical current for charging a battery within the handle. A first control 108 is operator adjustable by rotation and controls an intensity of the projected beam of light, and/or may turn the beam on and off. A second control 110 is operator adjustable by rotation and controls a width across a light beam. A third control 112 is operator adjustable by rotation and controls a length across the light beam.

Figure 3A:
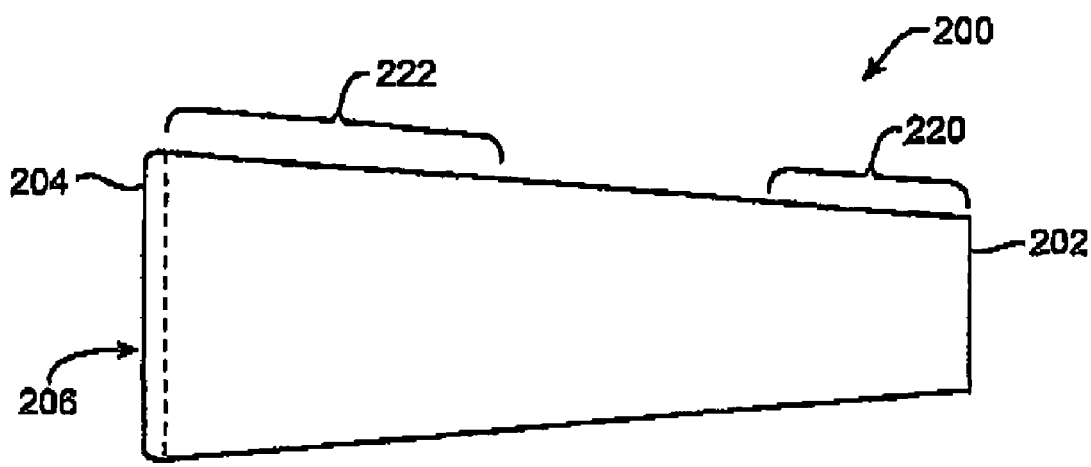
FIGS. 3A-3C illustrate a tubular sterile cover for use in the system and method of FIG. 1, in accordance with an embodiment of the invention.

Referring now to FIG. 3A, an exemplary sterile cover 200 comprises a flexible tapering tube having a proximal end 202 and a distal end 204 with an opening or lumen 206 extending therebetween. The ends of tubular membrane 200 are open, and the illustration of FIG. 3A generally shows the membrane in a flat configuration with distal end 204 expanded to its maximum size. In this configuration, proximal end 202 has a width of about 2 inches, while distal end 204 has a flat width of about 3.5 inches (providing a diameter of between about 1.5 to 2.25 inches).

Figure 3B:
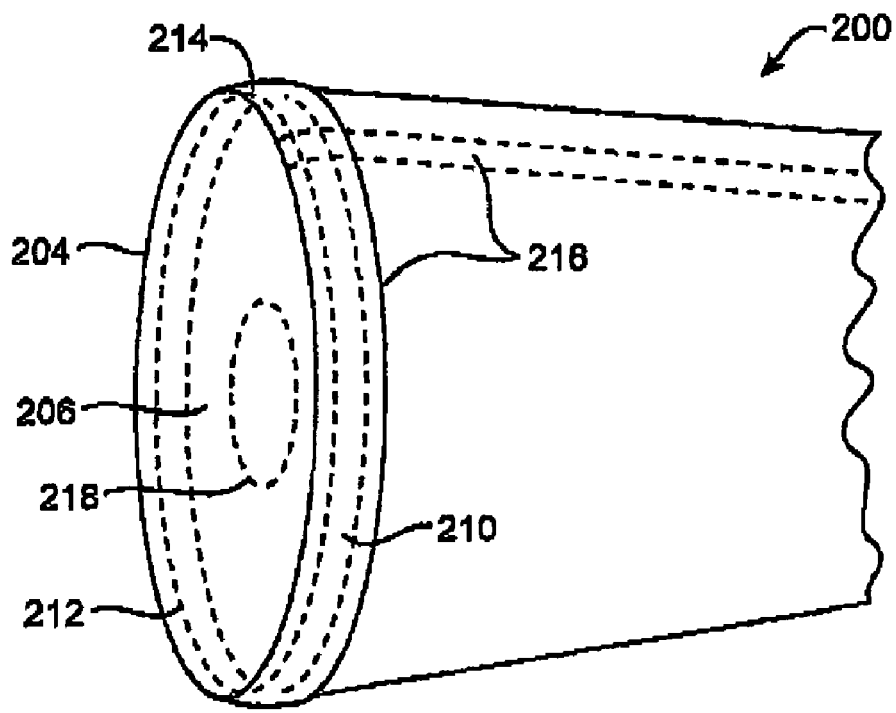
Figure 3C:
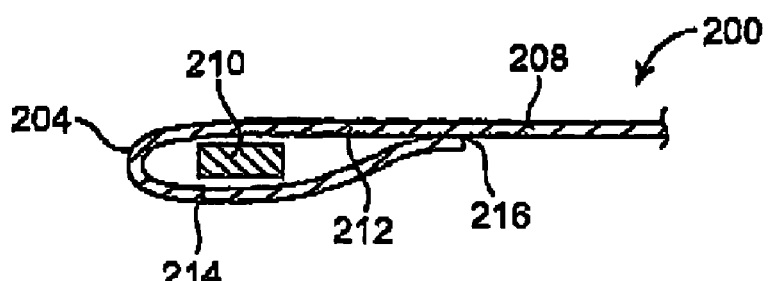

As illustrated in FIGS. 3A, 3B, and 3C, distal end 204 of tubular membrane 200 may be defined by a fold in the membrane material 208. An elastomeric band 210 may be disposed between an inner layer 212 of the material and an outer layer 214 of the membrane material. Seams 216 may be fused, adhesively bonded, heat-welded, fastened, or the like, and the fold may be inwardly oriented or outwardly oriented.

Elastomeric band 210 is substantially coextensive in size with distal end 204, and is expandable to an enlarged configuration which receives the proximal end of the slit lamp handle therethrough. Elastomeric band 210 may be resiliently biased toward a small configuration 218, providing distal end 204 with a small configuration cross-section that is sufficiently small to engage a the slit lamp distally of the handle and proximally of the slit-light window. This allows elastomeric band 210 to help restrain tubular membrane 200 over the handle and inhibit proximal movement of distal end 204, while allowing easy removal and replacement of the cover.

Referring once again to FIG. 3A, a proximal portion 220 of tubular membrane 200 preferably fits sufficiently tightly around a proximal portion of the slit lamp handle to inhibit distal movement of proximal end 202. The hand of the slit lamp operator may optionally engage proximal portion 202 when grasping the slit lamp so as to provide accurate control over the orientation and movement of the slit lamp.

A distal portion 222 of tubular membrane 200 adjacent distal end 204 preferably has a size significantly larger than the adjacent slit lamp handle when the slit lamp is disposed therein to facilitate manual manipulation of variable position sliding switches of the slit lamp handle. This allows the operator to control the light slit intensity, width, length, or the like. Preferably, the material of tubular membrane 200 is sufficiently strong to allow adjustment of the controls through the cover without tearing, but is soft enough to be easily pliable. The exemplary tapering tubular membrane has sufficient cross-sectional size adjacent the sliding switches to facilitate movement of the sliding switches by manipulation therethrough, the exemplary material of tubular membrane 200 inhibiting rustling and noises when the sliding switches are manipulated.

An exemplary membrane material for tubular membrane 200 comprises a polyurethane having a thickness in a range from about 1.0 mil to about 3.0 mil, ideally having a thickness of about 2 mil, and is commercially available from Ming Fai, located at Schenzchen, China. A wide variety of alternative supplier or specific materials may also be employed.

Figure 4:
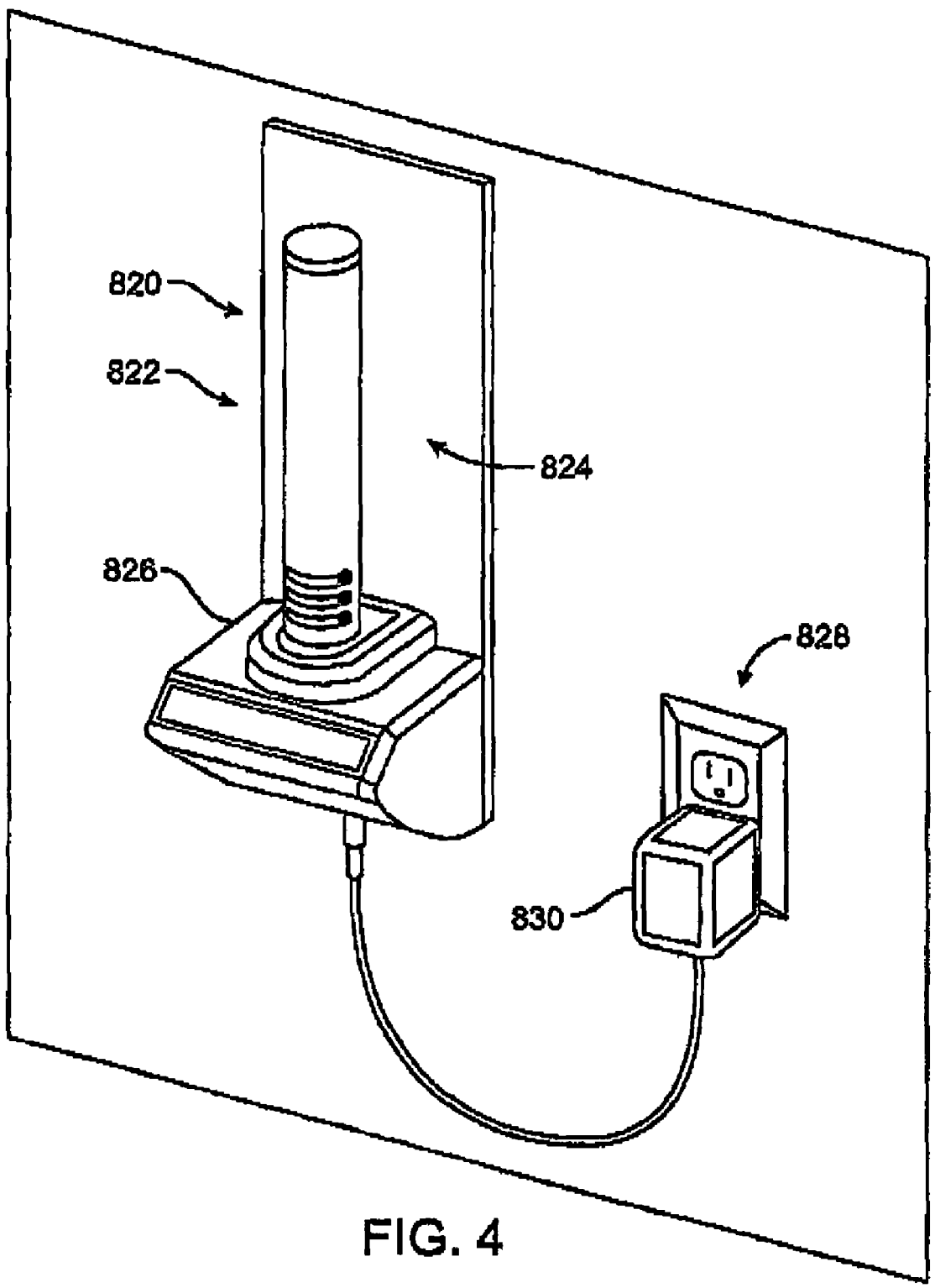
FIG. 4 illustrates an alternative wall mounted slit lamp for use with the cover of FIG. 3A, in accordance with an embodiment of the present invention.

Referring now to FIG. 4, a wall mounted slit lamp 820 for use with tubular membrane 200 is mounted to a wall 822. Wall mounted slit lamp 820 comprises a base 826 and a backing plate 824 for receiving another sterile cover. The sterile cover over backing plate 824 maintains sterility of the gloved operator as the operator grasps the handle of wall mounted slit lamp 820, while slit lamp 820 is covered by the sterile cover as described above. In some embodiments slit lamp base 826 comprises a holder for a spare bulb (not shown), a spare battery (not shown), or the like. The wall mounted slit lamp can be mounted to any vertical surface including a wall of an operating room, a vertical surface of the refractive laser system, or the like. The wall 822 preferably comprises a receptacle 828 for receiving a power supply 830 of the wall mounted slit lamp.

As described in U.S. patent application Ser. No. 10/876, 268, alternative battery charging bases may be employed, with the charging bases optionally comprising stand alone structures, built in battery chargers integrated with the laser surgery system, or the like. Such charging bases may have a foot print envelope with dimensions that do not exceed a width of 4 inches, a length of 7 inches and a height of 5 inches, and a smart charger may be included within the charging base to prevent over charging of the battery. Suitable charging base may be approved by regulatory agencies to provide an ETL listing and a CE Mark certification. As an acronym, ETL stands for Electro-Technical Laboratory, and ETL SEMKO is a worldwide electrical safety testing and certification agency having offices located in San Francisco, Calif. ETL SEMKO is a division of INTERNEK TESTING SERVICES. ETL can certify medical products for compliance in global markets. The term CE Mark stands for CONFORMITÉEUROPÉAN and a product having such a mark conforms to safety and quality standards set forth by the European Community. Sterility of the charging base may be enhanced by a design that avoids compromising sterility of the head covered by the sterile cover as described above while a physician wearing sterile gloves reaches for and grasps the covered handle of the head of the slit lamp.

Figure 4A:
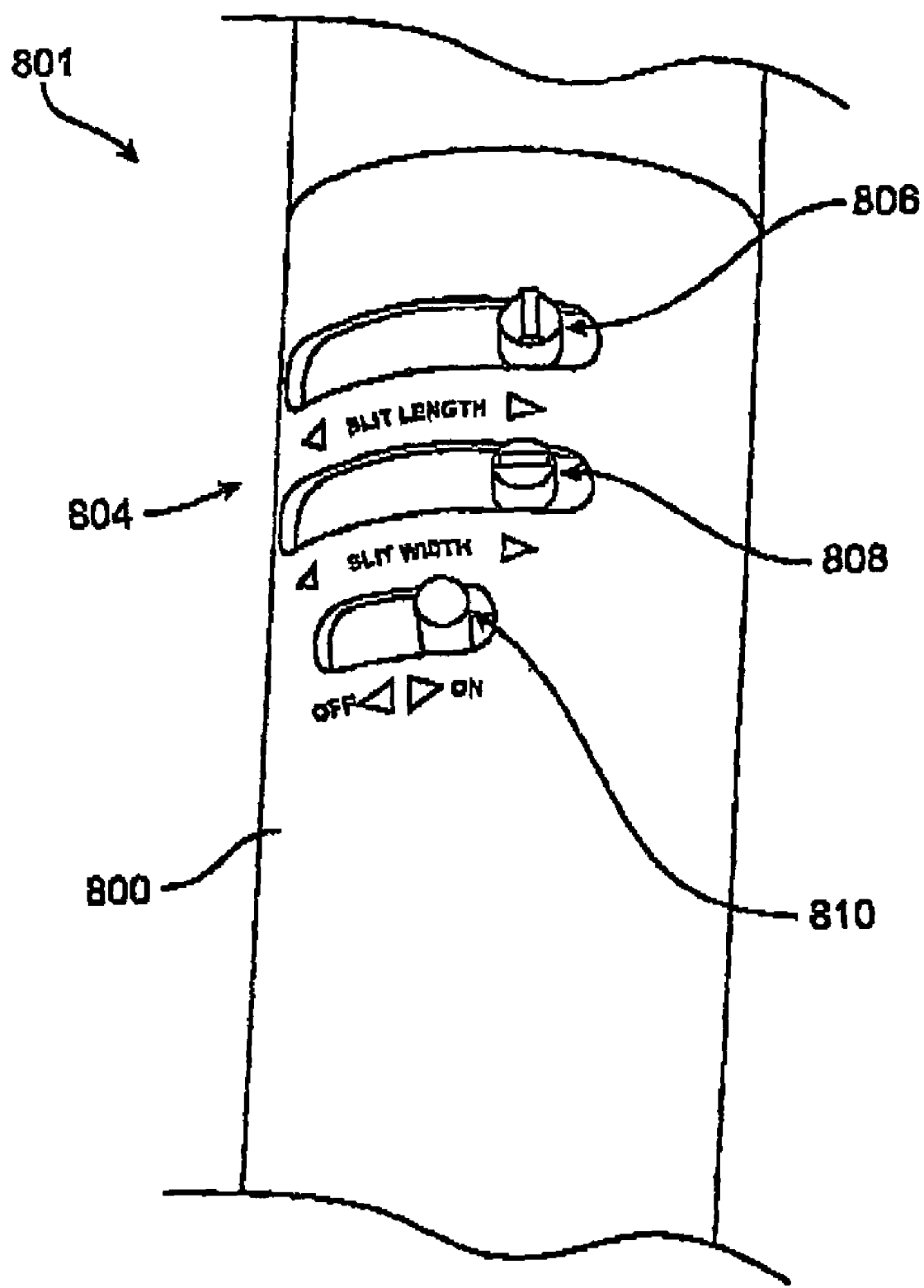
FIG. 4A illustrates slide controls of the slit lamp of FIG. 4, which can be manipulated through the cover of FIG. 3A in accordance with an embodiment of the present invention.
Figure 5:
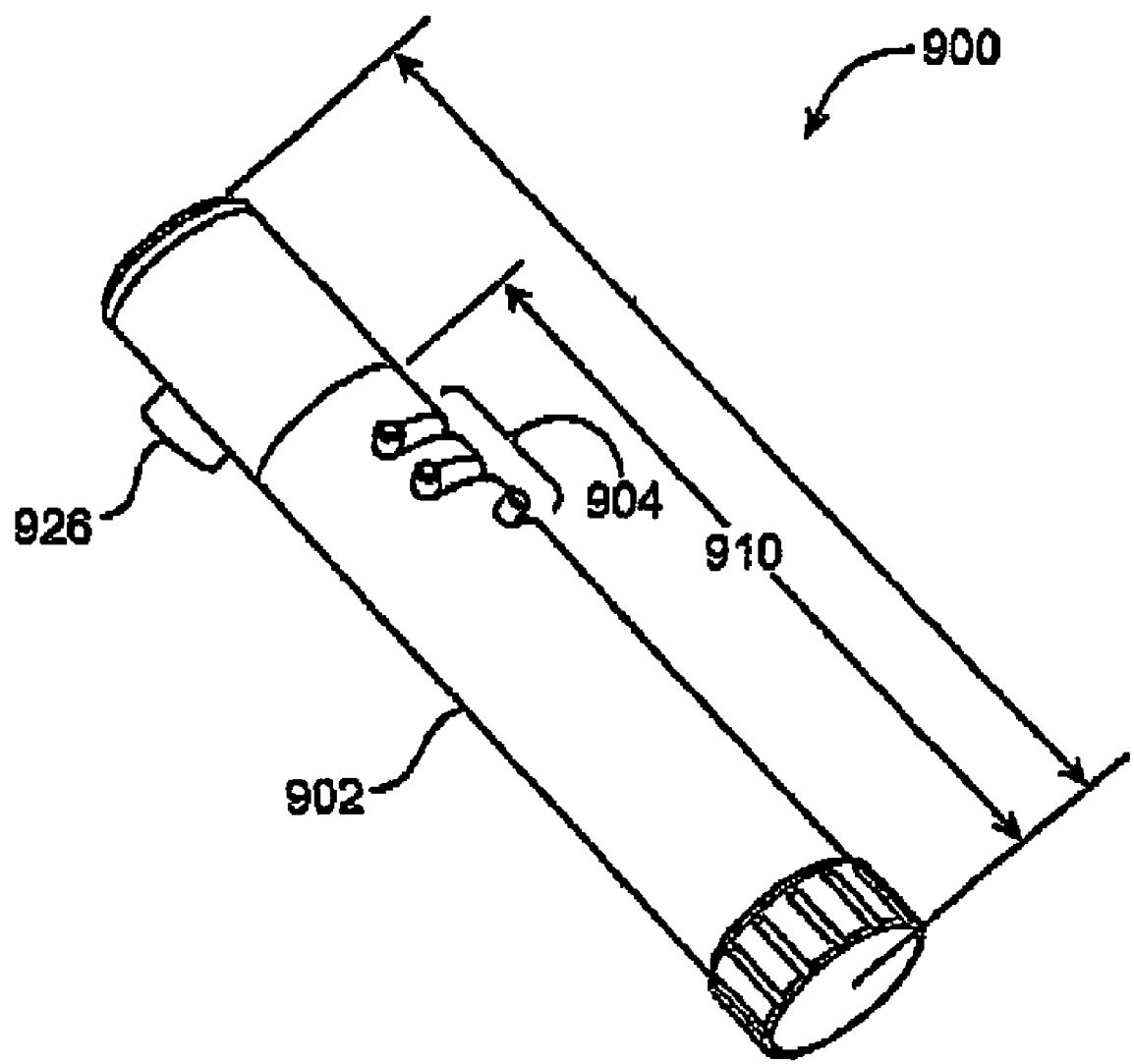
FIG. 5 is a perspective view illustrating a slit lamp similar to that of FIGS. 4 and 4A.
Figure 5A:
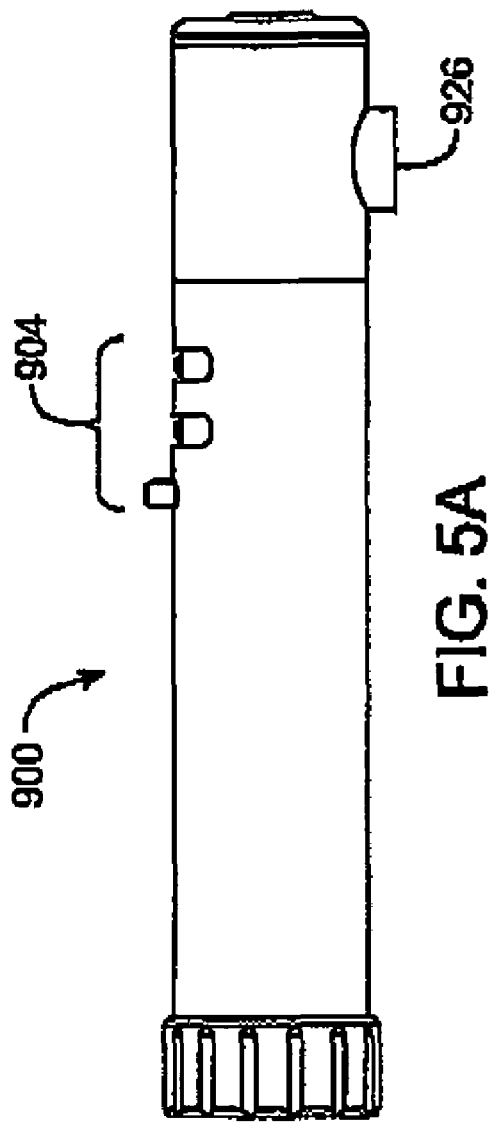
FIGS. 5A-5C illustrate a side view, a front view, and an end view, respectively, of the slit lamp of FIG. 5.
Figure 5B:
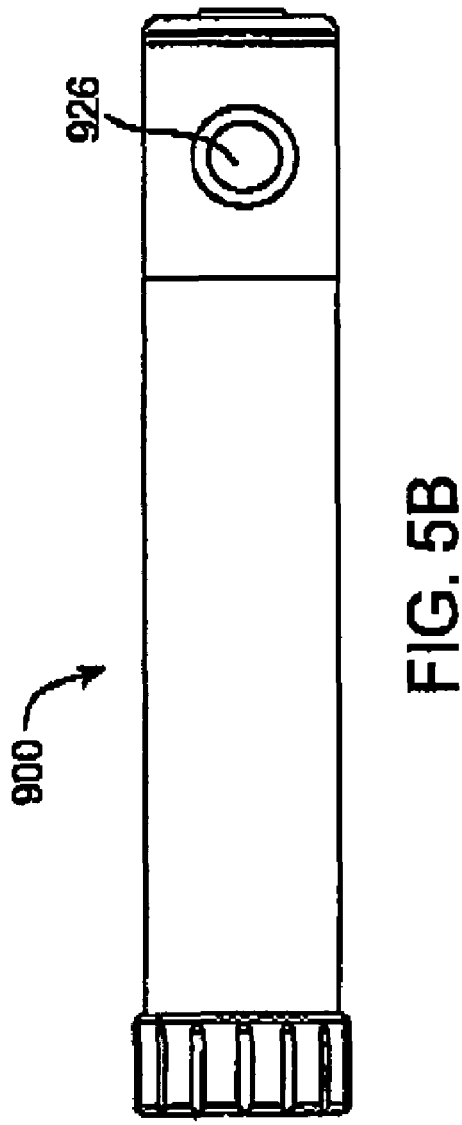
Figure 5C:
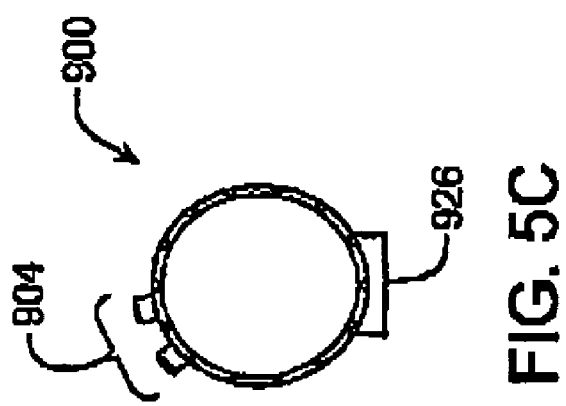

Referring now to FIG. 4A, exemplary slit lamp 801 comprises a handle 800 having a hand grip providing tactile orientation of slit lamp 801. Tactile orientation facilitates use by an operator wearing sterile gloves while a sterile cover covers the handle and the operator views the eye as described above. Slit lamp 801 may include, for example, grooves (not shown) aligned with a light transmitting window as described above, and thus aligned with the projected beam of light. Handle 800 also comprises controls 804 in the form of variable position slide switches for adjusting the length, the width and the intensity of the projected beam of light. The slit length across the projected beam of light is adjusted with the sliding control, the exemplary length control having a tactile feature comprising a vertical chisel point 806 aligned along an axis of the handle. The slit width across the projected beam of light is adjusted with a sliding switch having a horizontal chisel point 808 to provide an alternative tactile feed back to the operator. An intensity of the projected beam of light is controlled with the sliding control having a tactile feature comprising a rounded surface button point 810. By feeling these features of the slide switches, the operator determines that the control being adjusted controls the intensity of illumination, or the like. In a preferred embodiment button point 810 turns the slit lamp beam on and off, and controls 804 have friction which improve control by the gloved operator.

Figure 6A:
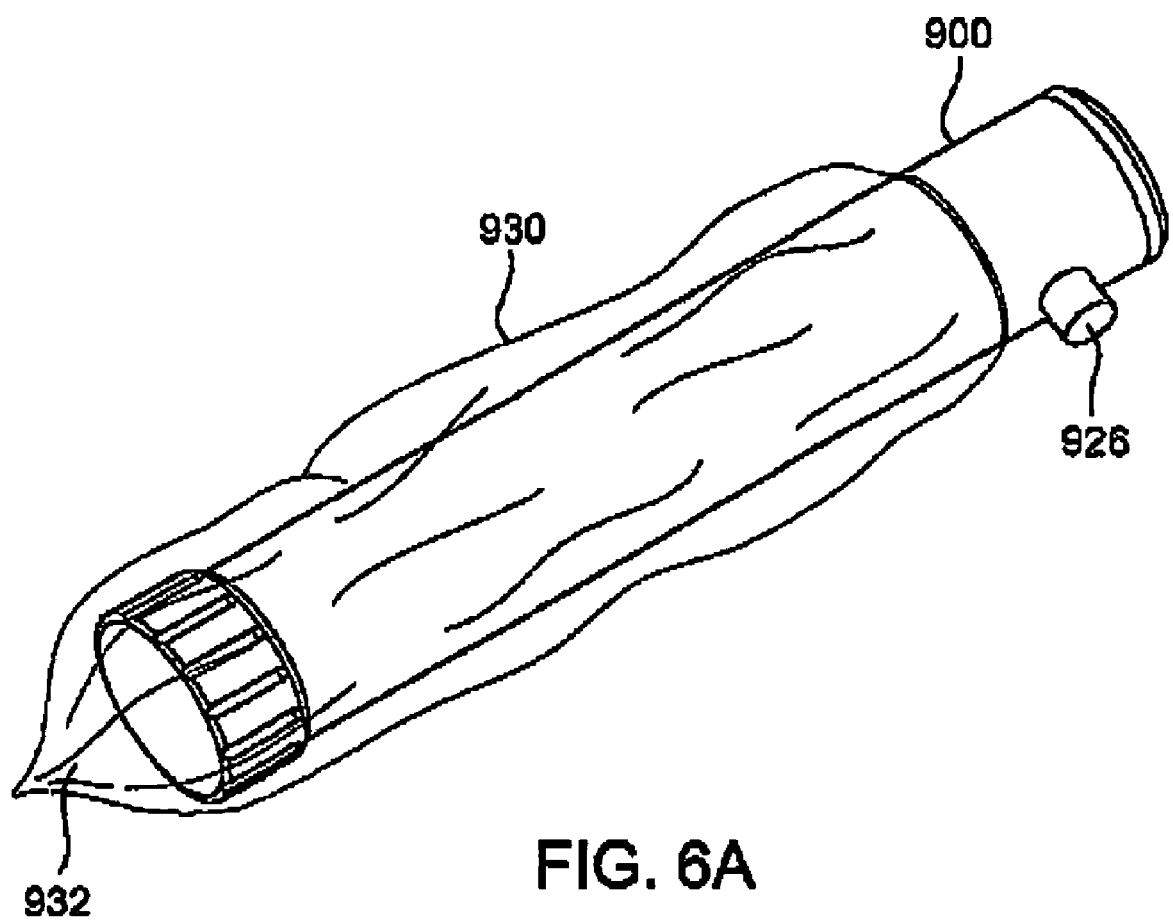
FIGS. 6A and 6B illustrate the slit lamp of FIG. 5 with an embodiment of the sterile barrier of the present invention disposed thereon.
Figure 6B:
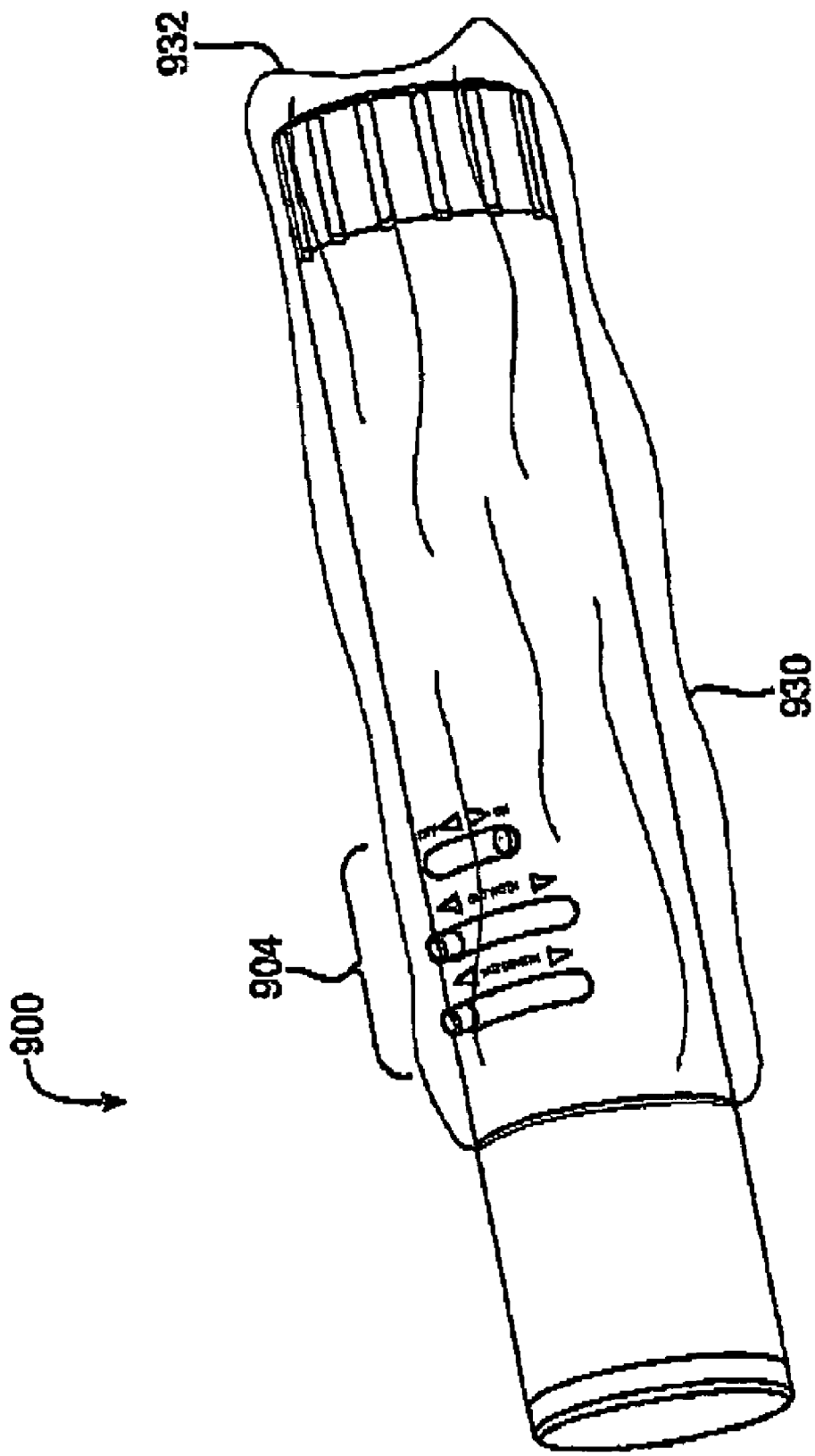

Another exemplary slit lamp 900 having a handle 902 for use in manaually positioning a slit-light window 926 is illustrated in FIGS. 5 and 5A-C. Variable position slide switches or controls 904 are also provided, with the controls here foregoing tactile differentiated end shapes. A handle 910 of slit lamp 900 and controls 904 are covered with a sterile cover 930 similar to those described above. In this embodiment, sterile cover 930 has a sealed proximal end 932, with the distal end of the sterile cover having a resilient band for inhibiting proximal movement of the cover from handle 910 of slit lamp 900, as illustrated in FIGS. 6A and 6B.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

What is claimed is:

1. A sterile barrier for use with a slit lamp, the slit lamp having a proximal handle and a distal light slit transmitting window, the sterile barrier comprising:
   a flexible tubular membrane having a distal first end, a proximal second end, and an opening therebetween, the opening extending through the first end;
   a resilient band attached to the first end of the tubular membrane so that an opening of the resilient band is substantially coextensive with the opening adjacent the first end, the resilient band having a relaxed configuration and a resiliently expanded configuration;
   the opening adjacent the first end and the resilient band in the resiliently expanded configuration being sufficiently large to receive the handle proximally therethrough; the opening adjacent the first end, when the resilient band is in the relaxed configuration, being as small as or smaller than a cross-section of the slit lamp between the handle and the window so that the band will releasably restrain the sterile barrier from moving proximally off the handle.

2. The sterile barrier of claim 1, the slit lamp having one or more slidable inputs for varying characteristics of slit light from the window, wherein the tubular membrane is configured for manual movement of the slidable inputs through the tubular membrane, and wherein the tubular membrane has a material that inhibits rustling sounds during manual slidable input movement.

3. The sterile barrier of claim 2, wherein the tubular membrane comprises a tapering tube of polyurethane, polyethylene, or cast polyethylene.

4. The sterile barrier of claim 2, wherein the tubular membrane comprises polyurethane.

5. The sterile barrier of claim 1, wherein the first end of the tubular membrane is defined by a fold, and wherein the resilient band is disposed between an inner layer of membrane material and an outer layer of membrane material, the inner and outer layers separated by the fold.

6. The sterile barrier of claim 1, wherein a proximal portion of the tubular membrane near the second opening fittingly receives the handle therein with sufficient tightness to facilitate secure manipulation of the slit lamp while grasping the handle through the proximal portion, and wherein a distal portion of the tubular membrane is sized to allow local movement of membrane material with movement of a variable-position sliding input of the slit lamp while the slit lamp adjacent the sliding input is disposed within the distal portion.

7. A method of comprising:
   inserting a handle of a slit lamp proximally through a first end of a flexible tubular flexible membrane; and
   restraining distal movement of the first end of the tubular membrane from the slit lamp by resilient forces between:
     the slit lamp disposed between the handle and a slit light transmitting window; and
     a resilient band of the tubular membrane.

* * * * *

UNITED STATES PATENT AND TRADEMARK OFFICE
CERTIFICATE OF CORRECTION

| | |
|---|---|
| PATENT NO. | : 7,422,328 B2 |
| APPLICATION NO. | : 11/123962 |
| DATED | : September 9, 2008 |
| INVENTOR(S) | : Amy B. Keller and John Weberg |

It is certified that error appears in the above-identified patent and that said Letters Patent is hereby corrected as shown below:

In the Claims:

Col. 6, lines 54-62 should read as follows:

Claim 7. A method of covering a hand held slit lamp with a sterile cover, the method comprising:
  inserting a handle of a slit lamp proximally through a first end of a flexible tubular membrane; and
  restraining distal movement of the first end of the tubular membrane from the slit lamp by resilient forces between:
    the slit lamp disposed between the handle and a slit light transmitting window; and
    a resilient band of the tubular membrane.

Signed and Sealed this
Ninth Day of July, 2013

Teresa Stanek Rea
*Acting Director of the United States Patent and Trademark Office*